(12) United States Patent
Masotti

(10) Patent No.: US 8,740,957 B2
(45) Date of Patent: Jun. 3, 2014

(54) DEVICE AND EQUIPMENT FOR TREATING TUMORS BY LASER THERMOTHERAPY

(75) Inventor: Leonardo Masotti, Florence (IT)

(73) Assignees: EL.EN. S.p.A., Calenzano, FI (IT); Esaote S.p.A., Cesale Monferrato (IT)

( * ) Notice: Subject to any disclaimer, the term of this patent is extended or adjusted under 35 U.S.C. 154(b) by 1450 days.

(21) Appl. No.: 11/423,080

(22) Filed: Jun. 8, 2006

(65) Prior Publication Data
US 2006/0253178 A1 Nov. 9, 2006

Related U.S. Application Data

(63) Continuation-in-part of application No. PCT/IT2004/000677, filed on Dec. 6, 2004.

(30) Foreign Application Priority Data

Dec. 10, 2003 (EP) ................................. 03425790

(51) Int. Cl.
*A61N 5/067* (2006.01)
(52) U.S. Cl.
USPC ............... 607/89; 607/88; 607/92; 606/13; 606/16
(58) Field of Classification Search
USPC .................... 607/88–92; 606/13–18
See application file for complete search history.

(56) References Cited

U.S. PATENT DOCUMENTS

| 4,612,938 | A | * | 9/1986 | Dietrich et al. ............... 600/476 |
| 4,672,963 | A | | 6/1987 | Barken |
| 4,807,633 | A | | 2/1989 | Fry |
| 4,929,246 | A | * | 5/1990 | Sinofsky ........................... 606/8 |
| 4,960,109 | A | | 10/1990 | Lele |
| 4,998,930 | A | | 3/1991 | Lundahl |
| 5,125,925 | A | | 6/1992 | Lundahl |
| 5,169,396 | A | | 12/1992 | Dowlatshahi et al. |
| 5,214,036 | A | | 5/1993 | Allison et al. |
| 5,222,953 | A | | 6/1993 | Dowlatshahi |
| 5,283,225 | A | | 2/1994 | Neumann et al. |
| 5,312,392 | A | | 5/1994 | Hofstetter et al. |
| 5,314,905 | A | | 5/1994 | Pandey et al. |
| 5,370,121 | A | | 12/1994 | Reichenberger et al. |

(Continued)

FOREIGN PATENT DOCUMENTS

| EP | 0367516 | 5/1990 |
| EP | 1341003 | 9/2003 |

(Continued)

OTHER PUBLICATIONS

Zahir Amin et al., Interstitial Laser Photocoagulation Therapy for Liver Tumors: Clinical Results; Proc. of SPIE vol. 1882, Laser-Tissue Interaction IV, ed. S L Jacques, A Katzir (Jul. 1993) Copyright SPIE.

*Primary Examiner* — Ahmed Farah
(74) *Attorney, Agent, or Firm* — McGlew and Tuttle, P.C.

(57) ABSTRACT

The device for interstitial laser thermotherapy of tumors comprises an hollow needle (3) with a point (3A) for perforating a tissue (T) to be treated, and a light guide (9) which can be inserted in said hollow needle. The hollow needle is associated with a membrane (17) which is inflatable to form a balloon (P) into which the distal end (9A) of said light guide (9) can project, the membrane being inflated to create a cavity in the tissue to be treated into which laser radiation is guided by said light guide.

30 Claims, 4 Drawing Sheets

(56) References Cited

U.S. PATENT DOCUMENTS

| | | | |
|---|---|---|---|
| 5,569,240 A | 10/1996 | Dowlatshahi et al. | |
| 5,657,760 A | 8/1997 | Ying et al. | |
| 5,861,020 A | 1/1999 | Schwarzmaier | |
| 5,891,133 A * | 4/1999 | Murphy-Chutorian | 606/7 |
| 5,989,246 A | 11/1999 | Kaufmann et al. | |
| 6,022,309 A | 2/2000 | Celliers et al. | |
| 6,283,958 B1 | 9/2001 | Vogl et al. | |
| 6,432,081 B1 | 8/2002 | Atala | |
| 6,464,693 B1 * | 10/2002 | Andrews et al. | 606/15 |
| 6,500,121 B1 | 12/2002 | Slayton et al. | |
| 6,519,376 B2 | 2/2003 | Biagi et al. | |
| 2003/0060813 A1 * | 3/2003 | Loeb et al. | 606/17 |

FOREIGN PATENT DOCUMENTS

| | | |
|---|---|---|
| GB | WO93/04727 | 3/1993 |
| IT | 1286836 | 3/1998 |
| WO | WO94/20037 | 9/1994 |
| WO | 97/39691 A | 10/1997 |
| WO | WO00/33913 | 6/2000 |
| WO | 03/065880 A2 | 8/2003 |

\* cited by examiner

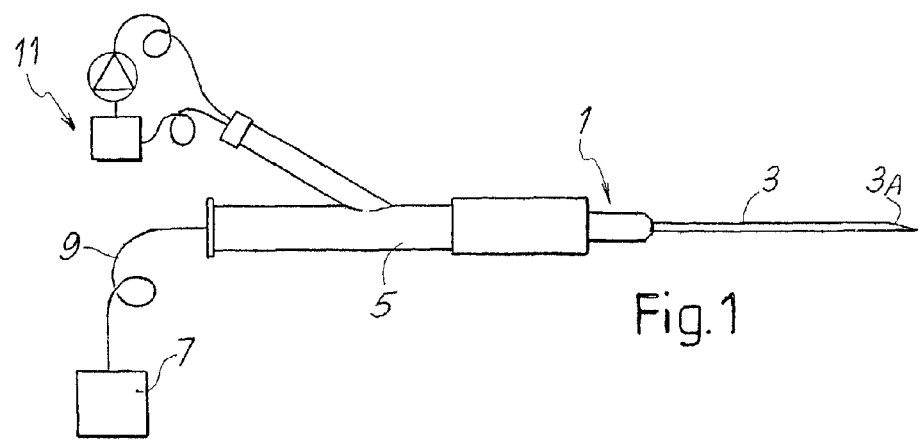
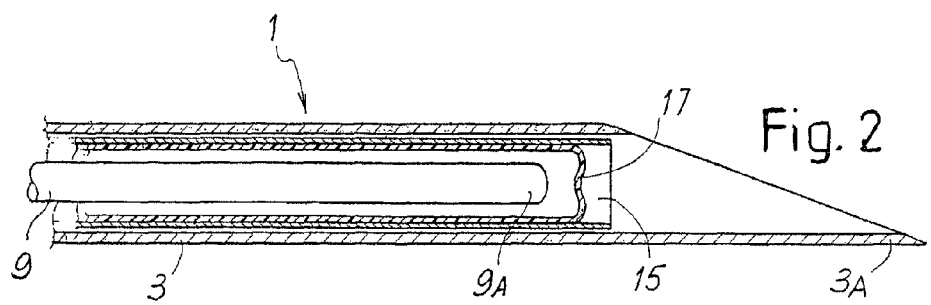
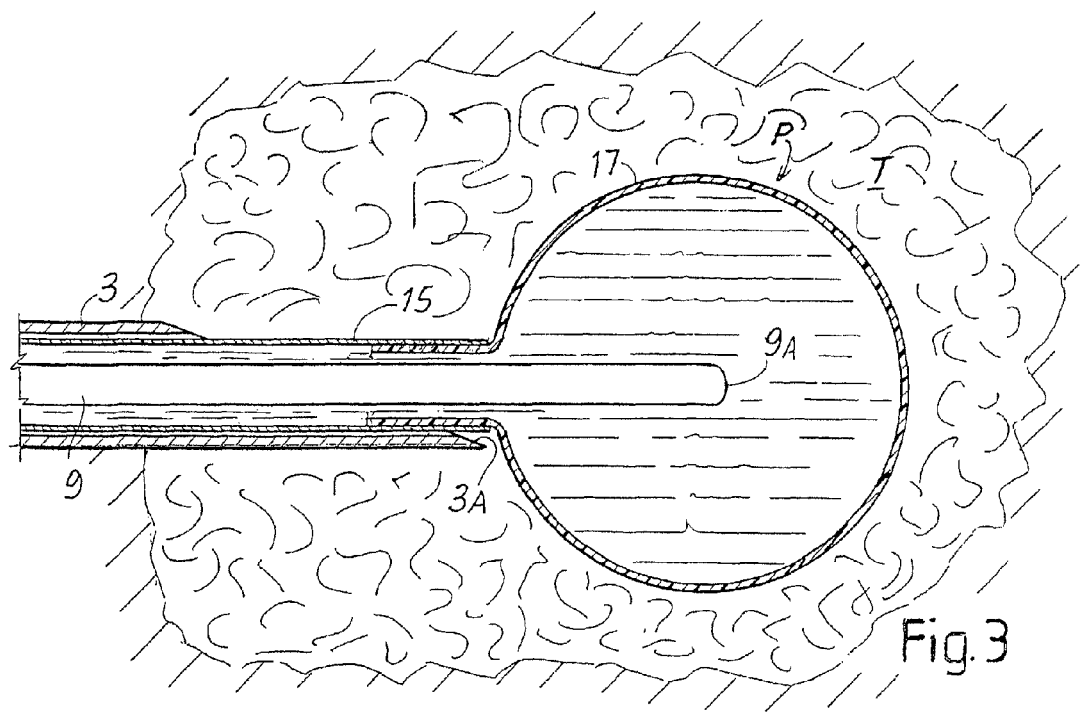

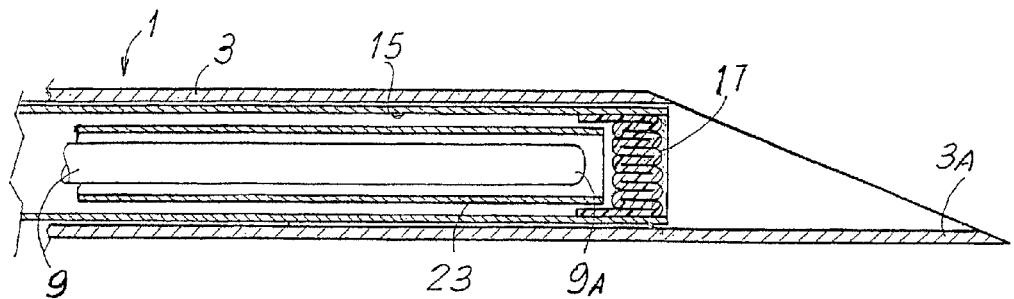
Fig. 4
Fig. 5
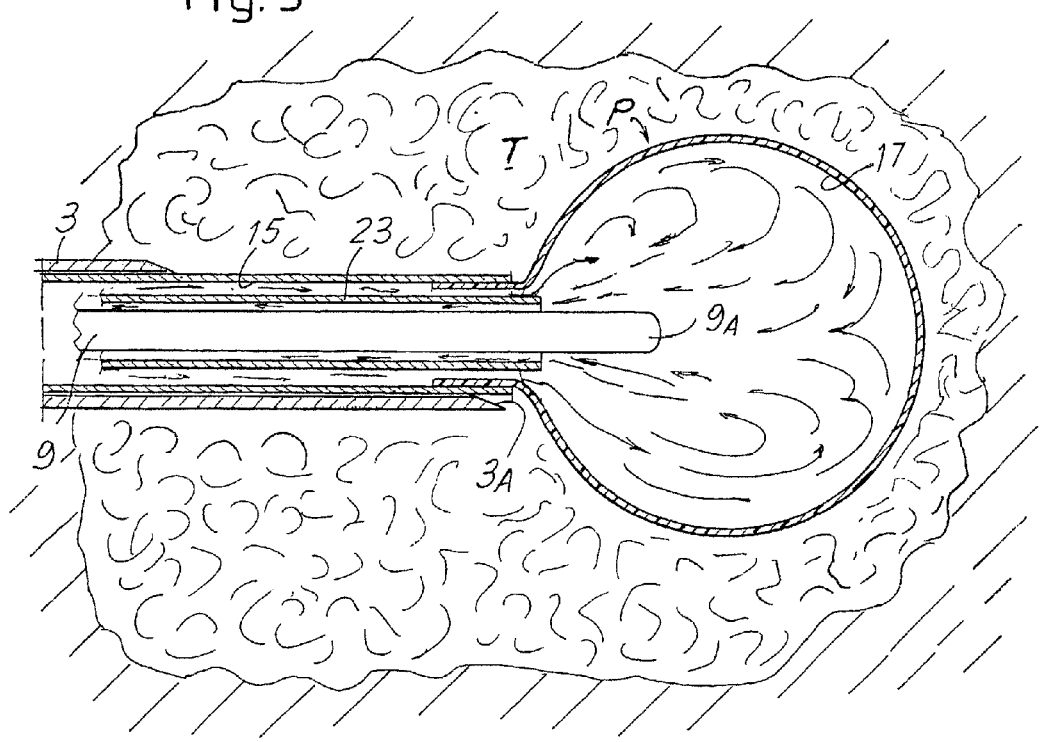

DEVICE AND EQUIPMENT FOR TREATING TUMORS BY LASER THERMOTHERAPY

CROSS REFERENCE TO RELATED APPLICATION

This is a continuation-in-part of and claims the benefit (35 U.S.C. §120 and 365(c)) of copending International Application PCT/IT2004/000677 of Dec. 6, 2004, which designated inter alia the United States and which claims the priority of European Application EP 03425790.7 of Dec. 10, 2003. The entire contents of each application is hereby incorporated by reference in its entirety.

TECHNICAL FIELD

The present invention relates to a device for treating tumor tissues by interstitial laser thermotherapy, also called interstitial laser photocoagulation therapy, in other words by applying heat to the tumor tissue in order to destroy the tumor cells by the effect of the hyperthermia generated by the laser energy absorbed by the tissues.

The invention also relates to equipment comprising a laser source and a device of the aforesaid type, and to a method of treatment.

BASIS OF THE INVENTION

It is known that tumor masses are particularly heat-sensitive, and therefore even modest temperature rises of 7-9° C. with respect to the base temperature can cause the destruction of tumor cells. This phenomenon has been studied and used for treating tumor masses while avoiding particularly invasive surgical removal operations, especially for the treatment of tumors in organs which are difficult to reach with conventional surgical techniques. One of the many articles dealing with this subject is Z. Amin et al., *Interstitial Laser Photocoagulation Therapy for Liver Tumors: Clinical Results*, in SPIE, Vol. 1882, Laser-Tissue Interaction IV, 1993, p. 202 ff.

In clinical applications, the therapy comprises the echograph-guided insertion of one or more hollow needles into the patient's body in order to reach the tumor tissue in the organ to be treated. When the treatment site is reached, an optical fiber is inserted into the needle to act as a light guide or wave guide for guiding into the treatment area the laser energy obtained from a suitable laser source. Continuous emission diode lasers or Nd:YAG lasers are typically used. The applied power is of the order of 2-6 W, and the application times are of the order of several minutes.

The energy emitted from the distal end of the fiber is absorbed by the surrounding tumor tissue and causes a temperature increase with consequent denaturing of the proteins and necrosis of said tissue. This form of treatment gives rise to a number of problems.

In the first place, the laser emission from the tip of the fiber is not isotropic, and therefore the resulting treatment is not uniform. In the second place, undesirable temperature profiles are generated in the tissue when ordinary optical fibers are used to inject the laser energy into the treatment area. In practice, the temperature rises markedly in the immediate vicinity of the end of the fiber, projecting from the hollow needle inserted into the tumor, but decreases rapidly as the distance from the fiber increases. The therapeutically effective temperature is therefore reached only in a very small volume, with a diameter of a few millimeters, around the position of the optical fiber.

In order to reach therapeutically effective temperatures, in other words those capable of inducing necrosis of tumor tissue, even at a greater distance from the end of the optical fiber, the temperature in the area immediately adjacent to the fiber would have to be increased excessively. Excessive temperatures cause damage to the fiber.

In any case, the high temperature in the proximity of the fiber causes phenomena of vaporization and carbonization of the surrounding tissue. Both of these phenomena reduce the penetration of the energy through the tissues required to reach areas more remote from the distal end of the fiber. Vaporization gives rise to a further drawback, in that it makes it difficult if not impossible to provide echographic monitoring of the position of the needle and the optical fiber and the effect of the treatment, since the water vapor impedes the propagation of ultrasound.

To overcome or mitigate these drawbacks, it has been suggested that a coolant liquid, typically a physiological solution, be introduced into the treated area. Examples of devices and therapeutic techniques based on this principle are described in U.S. Pat. No. 5,169,396, U.S. Pat. No. 5,222,953 and U.S. Pat. No. 5,569,240. The drawbacks of this procedure are apparent. The physiological solution remains inside the treated organ and can even lead to the undesired spread of tumor cells, causing the spread of the tumor.

U.S. Pat. No. 5,861,020 describes a device for laser treatment of tissues, in which a light guide is inserted into a duct closed at its distal end by a cap of material transparent to laser radiation to permit irradiation. Thus a closed circuit is formed for the circulation of a coolant liquid around the end of the light guide.

U.S. Pat. No. 5,312,392 describes a device and a method specifically dedicated to the treatment of benign prostate hyperplasia by laser irradiation. The device has a light guide for injecting diffuse laser radiation and a cap in the form of an hollow needle.

U.S. Pat. No. 5,989,246 describes an optical fiber device for irradiating tumor tissue with high-power laser radiation. A diffusion element is placed at the distal end of an optical fiber to form a radiation lobe. The fiber and the diffusion device are housed in a cannula closed at the distal end to allow the circulation of a coolant liquid.

U.S. Pat. No. 6,283,958 describes a kit for laser treatment by interstitial thermotherapy of tumors. The light guide is inserted through a catheter inside an hollow needle. A coolant liquid circulation system is also provided.

A different approach to the treatment of tumors by laser energy consists of what is called photodynamic therapy (PDT) or phototherapy. In this therapy, a photosensitive chemical compound is administered to the patient (orally or by injection), and is predominantly absorbed by the tumor tissue rather than by the healthy tissue. The tumor tissue is then irradiated with laser energy which is absorbed by the photosensitive compound. This causes a photochemical reaction resulting in the necrosis of the tumor tissue. The selective absorption of the photosensitive product causes selective destruction of the tumor tissue even with unfocused irradiation.

This therapy is described in a number of documents including U.S. Pat. No. 5,214,036, U.S. Pat. No. 5,283,225 and U.S. Pat. No. 5,314,905, which describe specific products for this application.

Photodynamic therapy is used particularly for the treatment of tumors, including small and very small tumors, in hollow organs such as the urinary bladder. In this case, an optical fiber is inserted into the hollow organ to guide the laser radiation in order to irradiate the whole surface of the wall delimiting the cavity, for example the whole bladder. The administration of a photosensitive chemical compound before the laser treatment causes the laser radiation to interact with the compound absorbed solely by the tumor tissue present in the irradiated wall, and this causes localized necrosis of the tumor tissue.

In order to obtain more uniform irradiation of the bladder or other hollow organs subject to this form of treatment, a catheter carrying at its end a membrane forming a balloon which is inflatable by means of a liquid has been devised. This device is described in U.S. Pat. No. 5,125,925 and U.S. Pat. No. 4,998,930. The inflatable membrane has the function of distending the wall of the cavity to be irradiated, thus removing folds and shaded areas. Additionally, especially when it is made from flexible but inextensible material, it has the function of forcing the cavity to assume a shape which is as nearly spherical as possible. Thus, when the optical fiber is placed in the center of the cavity, substantially uniform irradiation of all points of the cavity wall is achieved.

Scattering media can be introduced into the liquid which inflates the cavity, these media providing fluorescent emissions when illuminated by the laser light guided by the fiber. The light produced by fluorescence has an intensity which is proportional to that of the primary radiation, and which, although much lower, is sufficient for detection by a photosensitive sensor for measuring the intensity and consequently the dose of primary energy supplied.

The catheter described in U.S. Pat. No. 5,125,925 is not suitable, and cannot be used, for interstitial thermotherapy.

U.S. Pat. No. 4,612,938 describes a further device and method for treating a cavity, for example the bladder, by photodynamic therapy. In this case, the bladder is distended by introducing a liquid containing scattering media directly into it. An optical fiber, inserted through a urethral catheter, permits the introduction of the liquid and also of an optical fiber which illuminates the wall of the bladder. The scattering media provide uniform illumination. In a specific embodiment, the liquid containing the scattering medium is not introduced into the cavity to be treated, but into a balloon fitted to the urethral catheter. These devices are also unsuitable for interstitial thermotherapy.

OBJECTS AND SUMMARY OF THE INVENTION

One object of the invention is to provide a device for interstitial laser thermotherapy of tumors which overcomes or mitigates one or more of the drawbacks of the known devices, and which enables a more effective treatment method to be used.

Another object of the invention is to provide laser equipment for interstitial thermotherapy which makes use of this device.

Essentially, the invention provides for the use of an hollow needle for penetrating into the tissue to be treated, this needle allowing a light guide, particularly an optical fiber, to be inserted coaxially with it, and being associated with an inflatable membrane into which the distal end of said light guide can project.

The inflatable membrane can be a flexible but substantially inextensible membrane. In this case, when it is inflated it forms a balloon of approximately spherical shape, subject to the surface stresses imposed by the surrounding tissue. However, it is also possible for the membrane to be deformable, in other words to increase its surface area under the internal pressure. The term "inflate" in the present description and the attached claims denotes both a condition of distension of the membrane without dilation and a distension and dilation of the membrane with an increase in its surface area.

With a device of this type, the needle is inserted through the patient's skin until it reaches the position of the tumor, penetrating into the tissue to be treated. This operation is advantageously monitored by an echographic, in other words an ultrasonic, system, using known procedures. When the needle has been inserted to the desired point, the membrane is extracted from the needle and inflated, by a liquid for example. The liquid can advantageously be physiologically acceptable, to prevent harm to the patient in case of accidental rupture of the membrane.

When inflated, the membrane compresses the surrounding tissue, creating a free area around the point of the needle. The dilating membrane essentially forms a kind of balloon, whose diameter can be of the order of 3-4 mm, but which can also be as much as 7-8 mm. The size of the hollow space formed in the treated tissue by the dilation of the membrane or balloon depends on the pressure used for the dilation fluid, but also, to a significant extent, on the greater or lesser deformability of the treated tissue.

Compression of the tissues surrounding the membrane following inflation thereof allows two positive effects to be achieved. On the one hand compressed tissue has a higher thermal transmission coefficient, i.e. heat conduction inside the tissue is increased and a more efficient treatment is achieved. On the other hand compression of the tissue also causes compression of the blood vessels and consequent reduction of the heat removal by blood circulation. Since a smaller amount of heat is removed by the blood circulating in the tissue surrounding the inflated membrane, more energy remains available for tissue treatment.

The light guide is inserted through the hollow needle until its distal end projects into the volume of the membrane. Thus, on the one hand, contact between the tissue to be treated and the light guide is avoided, while, on the other hand, a relatively large area of tissue, in other words the whole surface in contact with the outer surface of the membrane, is exposed to the light guide. This surface is essentially approximately spherical. The light radiation guided by the light guide thus irradiates the tumor tissue which is kept at a certain distance from the fiber, thus avoiding an excessive rise of temperature and consequent vaporization or carbonization of the body of tissue adjacent to the fiber. This effect of reducing the temperature of the tissue which initially comes into contact with the radiation is additionally due to the lower intensity striking the tissue, since the intensity of the radiation varies with the inverse of the square of distance, and therefore the wall of the balloon emits radiation with a lower value of power per unit of area, in other words of intensity. However, with a power of the order of 2-6 W (equal to that normally used for this form of therapy) the tumor tissue compressed by the dilated membrane is irradiated sufficiently to be heated, by absorption of the incident laser energy, to the temperature required for tissue necrosis.

As well as avoiding carbonization and/or vaporization of the tissues and overheating of the terminal part of the fiber, the device according to the invention also has the advantage of providing more extensive treatment for each penetration, owing to the large area irradiated.

In an advantageous embodiment, the device can comprise a system for circulating a fluid in the membrane when said membrane is inflated. In general, the circulating fluid is advantageously the same liquid as that used to dilate or inflate the membrane. Circulation of the liquid can be used, for example, to keep the temperature of the surrounding tissue under control, preventing it from exceeding levels which can cause carbonization. This can be useful, for example, when the treated tissue is relatively uncompressible and therefore the volume of the inflated membrane is small. Any means can be used for circulating the fluid, for example two ducts coaxial with the light guide, one for supplying the liquid and one for its return.

The end of the fiber can be suitably shaped, in a known way, to provide irradiation which is as isotropic as possible, and thus to irradiate the whole surface of the tissue in contact with the dilated membrane. However, this effect of isotropy can also be improved by inserting a light scattering medium, in other words a medium consisting of particles reflecting incident light, into the fluid which inflates the membrane. Thus an effect of integration of the light radiation is obtained, with a greater uniformity of power per unit of surface area over the whole irradiated surface. The presence of diffusing particles, in other words scattering media, in the volume of liquid filling the balloon formed by the membrane and surrounding the terminal end of the fiber has the additional purpose of creating on the surface of the membrane a laser energy radiation with a lower density than that which would be emitted directly by the tip of the fiber for the same injected power. Thus the temperature of the fiber and the density of the energy striking the tissue adjacent to the balloon formed by the membrane and that at greater depth are kept at controllable levels.

In general, the heating and the effect of hyperthermia on the tissues are achieved by the conversion of the laser energy to thermal energy in the irradiated tissues. However, it is possible for different energy transfer mechanism to be used. For example, a light-absorbing medium can be introduced into the liquid which inflates the membrane. This medium can consist of particles suspended in the fluid. These absorb the laser radiation and are heated. Thus thermal energy is directly transferred through the membrane of the device to the surrounding tissue, in addition to light energy. Ultimately, the whole of the light energy could be converted to thermal energy and reach the tissues solely in this form. In this case, the membrane, which is transparent or translucent at the laser wavelength when the tissues are irradiated directly, can also be opaque, and can be made from a material with a high thermal transmission coefficient.

It is also possible to introduce both absorbent particles and diffusing or scattering particles into the balloon formed by the dilated membrane. The presence in the membrane of a mixture of particles having different functions enables the device to act as a laser radiator with a low energy density and also as a controlled-temperature thermal radiator.

A further arrangement for obtaining greater uniformity of emission from the balloon formed by the dilated membrane and protection of the membrane itself consists in treating the tip of the optical fiber forming the light guide in such a way that it can radiate laterally over a length of several millimeters, as well as from the tip.

In an alternative embodiment, the distal end of the optical fiber forming the light guide can be provided with an opto-acoustic transducer, which converts the incident laser energy supplied by a pulsed laser to thermal energy and then (as a result of the pulsed dilation caused by the intermittent heating due to the pulsed laser energy) to ultrasonic waves. These are propagated through the liquid which inflates the membrane, and strike the membrane, transferring to it and then to the surrounding tissue the energy of the impact waves, which is again converted to thermal energy. An example of an embodiment of an optical fiber with an opto-acoustic transducer of this type is described in U.S. Pat. No. 6,519,376, the content of which is incorporated in full in the present description. The membrane is advantageously made from a material which allows the ultrasonic energy to pass to the tissues behind it.

The membrane can be housed in the hollow needle and can if necessary be associated with a cannula coaxial with the needle. On the other hand, it could be inserted into the needle, by means of a cannula for example, after the penetration of the needle into the tissue to be treated. For example, it is possible to provide a treatment kit comprising an hollow needle containing a probe to impede the penetration of tissue during the perforation. After the penetration of the needle to the requisite depth, the probe is removed and a cannula carrying the membrane at its distal end, or containing the membrane, in addition to any liquid circulation system that may be required. The light guide can be inserted coaxially with the cannula before or after its insertion into the needle. If necessary, other elements to be inserted coaxially with the perforation needle can be provided.

According to a different aspect, the invention relates to equipment for the treatment of tumors by interstitial laser thermotherapy, comprising a laser source, a light guide and an hollow needle for perforating a tissue to be treated, said light guide being designed to reach the tissue perforated by said needle. Characteristically, the needle is associated with an inflatable membrane, forming a balloon, into which the distal end of the light guide can project, to guide energy from the laser source into the internal space of said membrane. The light guide usually consists of an optical fiber.

In one advantageous embodiment, the laser source is a pulsed source. The pulses of the laser source are sufficiently narrow and sufficiently widely spaced to make the thermal relaxation constants smaller than the period of repetition of the pulses. Thus the excess temperature created in the tissues treated by the energy contributed by the pulse is dissipated between one pulse and the next, and the tissues surrounding the area which progressively undergoes the treatment returns to the vicinity of the base values before the next pulse is applied.

With this arrangement, the mean temperature of the tissues can be controlled so that it remains below levels which minimize or prevent carbonization and vapor production.

To control the temperature of the irradiated tissues while avoiding an excessive temperature rise, it is possible to vary the frequency of the pulses as well as their duty cycle. The values of one or other or both of these two parameters can also be modified according to the type of tissue treated, with allowance for the thermal relaxation constant which generally varies from one type of tissue to another. For example, the frequency of the pulses of the laser source can be in the range from 0.1 to 20 Hz, and the duty cycle of said pulses can be in the range from 5% to 50%.

The laser source is a source which emits at an optimal wavelength for the type of treatment. Different sources can be used, according to the type of tumor to be treated. Typically, use can be made of sources emitting in the range from 500 to 1500 nm and typically at 1064 nm, 810 nm, or 940 nm, or at other wavelengths in the visible and near infrared and in the infrared. Lasers suitable for these applications can be of the Nd:YAG or semiconductor types, or solid state lasers pumped by semiconductor or dye lasers.

Typically, each laser pulse can have an energy in the range from 300 mJ to 10 J. The energy level can also be chosen according to the size of the balloon formed by the dilation of the membrane associated with the hollow needle. Advantageously, the energy is such that there is an energy density in the range from 0.1 $J/cm^2$ to 20 $J/cm^2$ on the surface of the tissue in contact with the membrane.

For the purposes indicated above, the equipment can comprise a system for circulating a fluid, usually a liquid, in the membrane.

With a device and equipment of the type described above, it is possible to implement a method for treating a tumor tissue by interstitial laser thermotherapy, comprising the stages of:

perforating the organ with an hollow needle until the point of said hollow needle is brought into the interior of the tumor tissue to be treated;

inserting an inflatable membrane into the perforated tissue;

inflating said membrane with a fluid, dilating the perforation formed by the hollow needle and moving the tissues away from the central area of the membrane;

guiding laser energy from a laser source to the interior of the said membrane.

BRIEF DESCRIPTION OF THE DRAWINGS

The invention will be more clearly understood from the description and the attached drawings, which show embodiments of the invention provided by way of example and without restrictive intent. More particularly, in the drawing, FIG. 1 shows a schematic diagram of the equipment;

FIG. 2 shows a longitudinal section through the terminal part of the device, in a first embodiment;

FIG. 3 shows a section similar to the section of FIG. 2 in operating conditions;

FIG. 4 shows a longitudinal section through the terminal part of the device, in a second embodiment;

FIG. 5 shows a section similar to the section of FIG. 4 in operating conditions;

DETAILED DESCRIPTION OF EMBODIMENTS OF THE INVENTION

Figure 6:
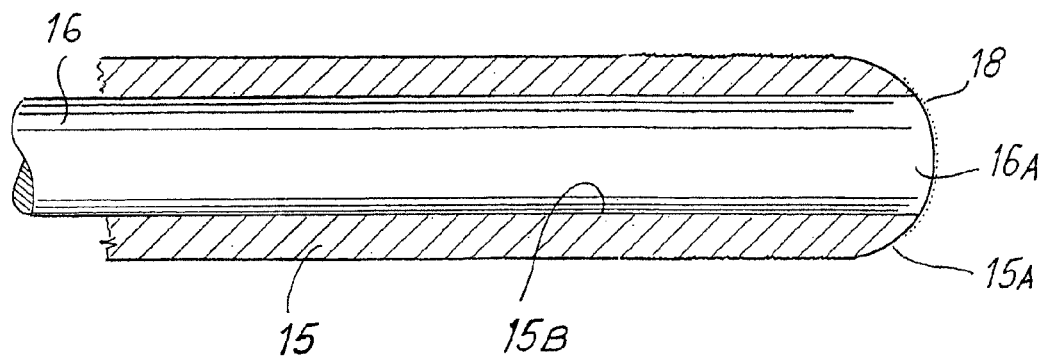
FIGS. 6 to 8 show a further embodiment of a device according to the invention and its production.

FIG. 1 shows in a general and schematic way equipment according to the invention. Reference 1 indicates the whole of a device provided with an hollow needle 3 having a point 3A sharpened to penetrate into the tissues of the patient until it reaches the tumor to be treated. The device 1, which will be described in greater detail in the following text, is connected to a laser source 7 by means of a Y connection indicated schematically by 5. The laser radiation emitted by the laser source 7 is guided by a light guide consisting of an optical fiber 9 towards and through the device 1 and the hollow needle 3.

The other branch of the Y connection 5 is connected to a pumping system indicated schematically by 11. The pumping system 11 is used to introduce a liquid into the device 1 at a sufficient pressure to expand a membrane forming a balloon which has to be at least partially dilated inside the tissue to be treated, as described in greater detail below. The pumping system 11 can also be used to keep the fluid in circulation.

In the example illustrated in FIGS. 2 and 3, the device 1 comprises a cannula 15, inserted coaxially in the hollow needle 3, this cannula housing a flexible, and if necessary extensible, membrane 17. The membrane 17 can be made from latex or other suitable material, and can be folded in an appropriate way to be housed in the cannula 15. The materials and folding systems of the membrane can be similar to those used in angioplasty catheters.

The optical fiber 9, whose distal or terminal end, in other words the end opposite the end into which laser energy is injected from the source 7, is indicated by 9A, is positioned inside the membrane 17 and coaxially with the cannula 15.

The use of the device described above is disclosed in the following text with reference to FIG. 3. The hollow needle 3 is made to penetrate through the patient's skin until it reaches the tumor mass to be treated, represented schematically by T in FIG. 3. The point 3A of the needle 3 is represented in the figures as a simple oblique tip, but it could also be shaped differently, in a way known to those skilled in the art.

The penetration of the needle is monitored by an echographic probe, by a method substantially equivalent to that used at the present time in interstitial thermal treatment of tumors. By means of this probe, the position of the needle with respect to the position of the tumor T can be observed on the echograph monitor, so that the point of the needle can be stopped in the desired position.

When this position is reached, the needle can be withdrawn slightly and/or the cannula 15 can be made to project from the needle, in such a way that its terminal edge is advantageously positioned beyond the point 3A of the needle 3. A liquid at the requisite pressure is then introduced by means of the pumping system 11 into the membrane 17, which is inflated, being distended and possibly dilated, to take the shape of a balloon P. The pressure of the liquid inside the membrane 17 causes the compression of the tissue T. Having been perforated by the needle 3, the tissue is compressed to form the space which is filled by the balloon P. The diameter of the balloon P can be of the order of 3-4 mm, but can also be greater, of the order of 8 mm, according to the type of tissue and the pressure of the liquid pumped into the membrane.

At this point, the distal end 9A of the optical fiber 9 is inserted approximately up to the center of the balloon P. These operations are also monitored by the echograph so that the fiber can be made to reach the desired position.

The distal end 9A of the fiber 9 is shaped in such a way as to emit within the largest possible solid angle, thus reducing the shaded areas. If necessary, the final millimeters of the optical fiber 9 can be treated to provide lateral emission, in such a way that the whole approximately spherical surface of the balloon P is irradiated.

Even when, e.g. due to the rigidity of the tumor tissue, the diameter of the balloon P is limited to a few millimeters, the area of tissue exposed to the fiber is much greater than the area normally found to be in contact with a fiber inserted directly into an hollow needle in contact with the tissue to be treated. Furthermore, the tissue T is not in contact with the fiber. Both of these factors are positive, because:

the area and consequently the volume treated on each penetration of the needle 3 are increased;

the temperature of the tissue, including that closest to the fiber, is reduced, thus avoiding phenomena of vaporization and/or carbonization;

damage to the fiber due to contact with the tissue is avoided.

To avoid phenomena of overheating of the layer of tissue T in contact with the membrane 17, the laser source 7 is advantageously a pulsed source. It can comprise a solid state Nd:YAG laser, a semiconductor laser, with an optical fiber, having a visible, near infrared or infrared wavelength, this wavelength being in the range from 500 nm to 1500 nm in continuous mode or in pulsed mode with a repetition frequency in the range from 0.1 Hz to 20 Hz, a duty cycle in the range from 5% to 50%, a power of 2 W to 10 W, a pulse energy of 300 mJ to 10 J, and an energy density delivered to the tissue in the range from 0.1 $J/cm^2$ to 20 $J/cm^2$.

FIGS. 4 and 5 show a modified embodiment of the terminal part of the device. Identical numbers indicate parts identical or equivalent to those of the preceding example of embodiment. In this case, the membrane 17 is connected to the terminal portion of the cannula 15. The procedures for inserting the needle 3 into the tumor mass are similar to those described above. In addition to the members and elements illustrated previously, the device of FIGS. 4 and 5 also has a second cannula 23 located inside the cannula 15 and coaxially with it. The optical fiber 9 is inserted coaxially into the second cannula, or inner cannula, 23. An annular passage is formed between the cannula 15 and the inner cannula 23 for the introduction of the liquid for distending the membrane 17. A second annular passage is formed between the inner cannula 23 and the optical fiber 9. This second annular passage is used for the return of the liquid introduced through the annular passage between the cannulas 15 and 23.

With this configuration (or another equivalent configuration) a liquid can be circulated in the inner volume of the balloon P, as diagrammatically indicated the arrows of FIG. 5. The liquid can be kept at a controlled temperature, in such a way that the temperature of the tissues and of the fiber 9 is limited. A heat exchanger and a thermostat located externally, in the liquid circulation circuit, advantageously keep the liquid at a controlled temperature.

To keep the temperature of the treated tissues under control, it is also possible to use an echographic system, in other words one based on the fact that the velocity of propagation of ultrasound is a function of the temperature. In this case, it is also possible to provide a feedback loop which, according to the temperature detected automatically by an ultrasonic probe, controls the emission conditions of the laser source which supplies the energy to the optical fiber. For example, the control loop can act on the duty cycle, on the repetition frequency of the pulses of the laser source (when this is pulsed) or on other control parameters of the laser source.

In the illustrated examples, a cannula 15 is provided, with the primary purpose of preventing damage to the membrane by the point of the needle. However, it is also possible to provide a device without this cannula, in order to reduce the diameter of the needle and thus make the operation less invasive.

Figure 7:
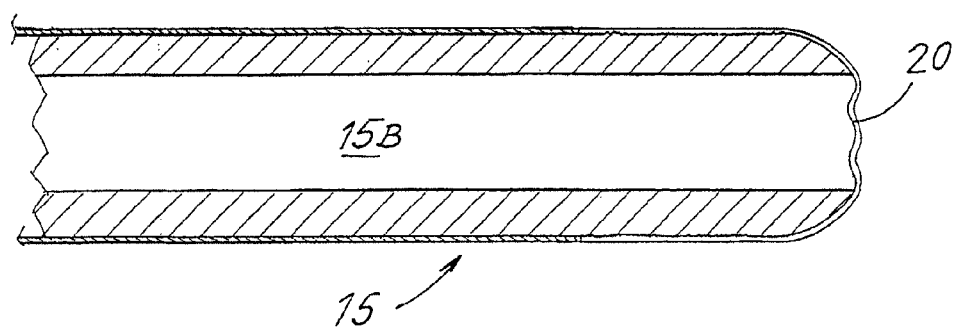
Figure 8:
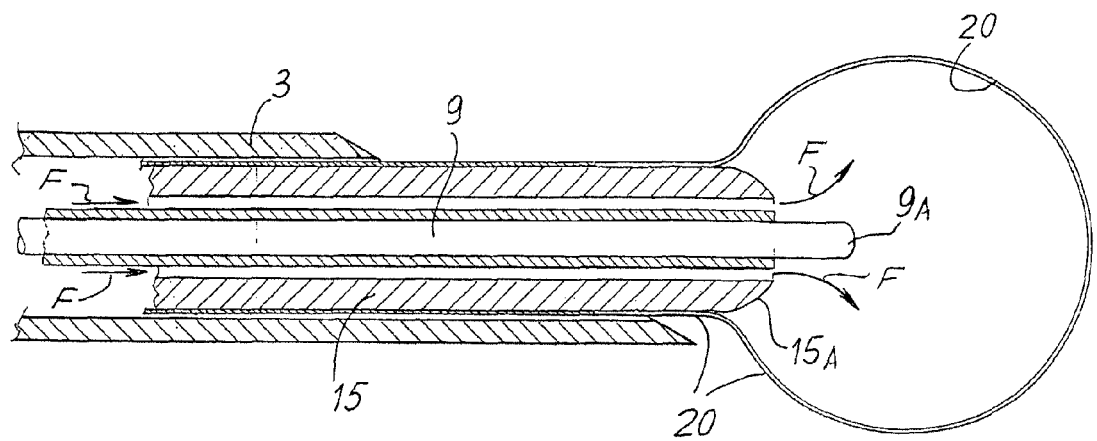

FIGS. 6 to 8 show steps for the manufacturing and use of a device according to the invention in a further embodiment. According to FIG. 6, a cannula 15 is provided, with a rounded tip 15A. The cannula is internally hollow (at 15B). A forming mandrel 16 is introduced into the cavity 15B of the cannula, the mandrel having an outer diameter substantially corresponding to the inner diameter of cannula 15. The forming mandrel 16 has a rounded tip 16A, the diameter of which substantially corresponds to the diameter of the rounded tip 15A of cannula 16. The tip of the mandrel is provided with a thin layer 18 of a detaching material.

The outer lateral surface of cannula 15 is textured to increase its roughness. A layer of natural latex or other elastic material is then formed on the tip of the cannula and around the distal portion thereof and the rounded tip of mandrel 16. The forming mandrel is subsequently removed from the cannula. The textured portion of the outer cannula surface provides reliable anchoring of the latex membrane to the cannula, while the detaching layer applied on the tip of the mandrel renders the removal of the mandrel easier without damaging the latex.

The result of this process is shown in FIG. 7. A hollow cannula 15 is obtained, provided with a latex membrane adhering to the end portion thereof. The membrane is expandable when a pressurized liquid or gas is introduced through the cannula. The outer surface of the cannula can finally be provided with a sheath of Teflon® or other suitable coating material to obtain a smooth and regular outer surface. The coating material has a low coefficient of friction to make sliding of the cannula 15 into the needle 3 easier.

The cannula provided with the latex membrane and the outer coating is introduced into a hollow needle 3, while an optical fiber 9 is introduced into the cannula, as shown in FIG. 8. The diameter of the optical fiber 9 is smaller than the inner diameter of the cannula 15, such that sufficient space is left there between for feeding a fluid which is used to inflate the membrane 20 by means of a fluid F.

In use, the cannula 15 is firstly retained entirely within the hollow needle 3. The latter is used to pierce the tissues of the patient's body and the tip thereof is advanced until the tissue to be treated is reached. Once the needle has reached the tissue to be laser-treated, it can be slightly retracted and the distal end of cannula 15 is extracted from the tip of hollow needle 3, as shown in FIG. 8.

The tip of the optical fiber 9 is maintained within the cannula until the membrane 20 has been inflated by the pressurized fluid F, as described herein before. In this way the optical fiber does not damage the latex membrane 20. The pressure of the fluid fed in the membrane through the space left between the fiber 9 and the inner surface of cannula 15 causes the latex membrane to expand and assume the shape of a balloon as shown in FIG. 8. Upon inflating the membrane 20, the tip of the fiber 9 can be advanced into the inner volume of the balloon, e.g. until it reaches the center thereof, or else it can remain flush with the tip of the cannula.

As mentioned above, the laser treatment can be kept under control with an ultrasound imaging system. Ultrasound imaging can be used for different purposes, among which:
  positioning and moving the needle within the patient's tissue, to reach the tumor to be treated;
  controlling the progress of the treatment, i.e. determining whether the tissue being treated has actually reached necrosis;
  controlling the temperature of the tissue under treatment, to avoid formation of vapor which would hinder the further treatment of the tissue.

Ultrasound imaging can assist the operator in properly positioning the tip of the needle in the volume of the tumor to be treated and also in moving the needle from one area of the tumor to another area once treatment of the first portion of the tumor is completed.

The characteristics of the tissue can be determined by means of spectral analysis of an ultrasound signal (see e.g. EP-A-1341003, to which reference can be made for further information on spectral analysis techniques for recognition of tumor tissue). Spectral analysis can be used to locate the tumoral tissue and to determine whether the tumor tissue has indeed reached necrosis after thermal treatment.

As mentioned above, however, the generation of vapor as a consequence of excessive temperature increase caused by the energy supplied by the laser beam would make ultrasound imaging impossible. The vapor reflects almost completely the ultrasound waves due to the acoustic impedance gradient at the vapor/tissue interface. The device according to the invention increases the overall surface treated by the laser beam, thus reducing the risk of excessive local heating of the tissue and consequent vapor generation.

On the other hand, ultrasound imaging can be used to detect possible vapor generation and automatically or manually control laser emission to reduce the tissue temperature. In a first possible embodiment, the operator supervises the process on the screen of the ultrasound device and, should vapor appear, manually modifies the laser emission, e.g. reducing the duty cycle of a pulsed laser source or else the laser power.

According to an improved embodiment, a closed control loop is provided. The ultrasound device is able to determine, e.g. by means of a spectral analysis of the image signals, the generation of vapor in the tissue under treatment. If and when this occurs, a control unit modifies the laser emission parameters, e.g. the duty cycle or the power.

Figure 9:
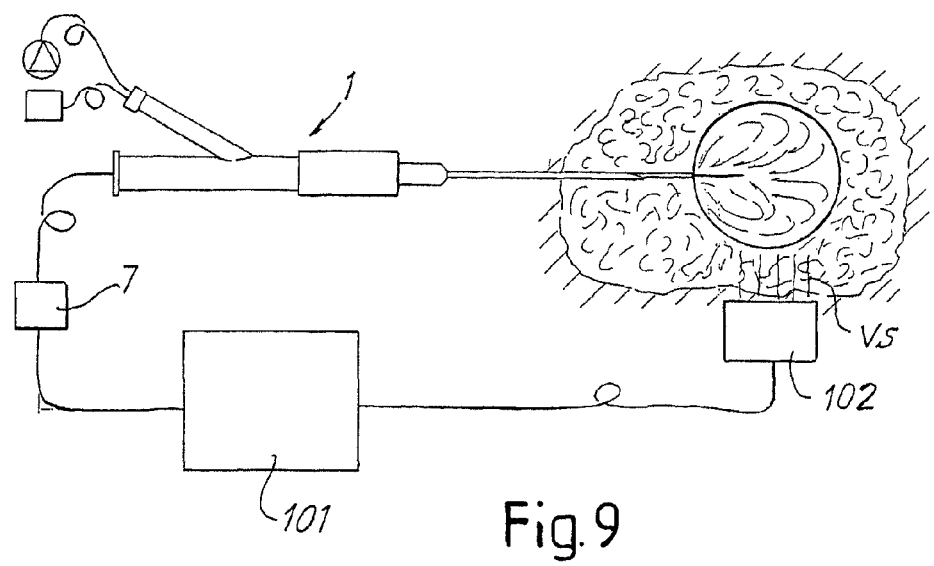
FIG. 9 shows a diagram of an equipment according to the invention, including ultrasound temperature control.

A block diagram of a system including the laser source and the ultrasound device is shown in FIG. 9. The ultrasound device is shown at 101. The ultrasound probe 102 is applied by the operator on the patient's body such that an ultrasound image of the tissue being treated is obtained. The treatment device is designated 1 as a whole and the laser source is shown at 7.

The use of ultrasound imaging for temperature measurement is known: see e.g. U.S. Pat. Nos. 6,500,121; 5,657,760; 4,960,109; 5,370,121; 4,807,633. This technique can be used in the present invention to monitor the tissue temperature in the volume under treatment. Vapor generation can be prevented by a closed loop control of the laser source, based on temperature monitoring.

An in vitro experimentation and an in vivo experimentation on animals can be used to determine the optimal treatment temperature ranges. Temperature thresholds can thereby be determined, which shall not be exceeded to avoid vapor generation. Once these values have been experimentally determined, the control software of the device can be implemented such as to control the laser source in order to keep the temperature of the tissue under treatment under the threshold, but above the temperature value needed to achieve necrosis of the tumor tissues.

Ultrasound applications for temperature control and for checking whether necrosis of the tumoral tissue has been achieved can be used also in combination with other energy sources, such as radiofrequency or ultrasound.

Clearly, the drawing shows only non-restrictive practical embodiments of the invention, which can be varied in its forms and arrangements without departure from the scope of the fundamental principle of the invention. Any reference numbers in the attached claims have the sole purpose of facilitating the reading of the claims with reference to the preceding description and to the attached drawings, and do not in any way limit their scope of protection.

What I claim is:

1. An interstitial tumor laser thermotherapy device, comprising:
    a hollow needle with a sharpened point configured for perforating a tissue to be treated;
    a light guide;
    a cannula arranged in said hollow needle such that said cannula is movable in said hollow needle to project from said sharpened point of said hollow needle, said light guide being inserted in said cannula, wherein said cannula is provided with an inflatable membrane which is inflatable to form a balloon into which the distal end of said light guide can project, the membrane being housed within said cannula or adherent to said cannula and said membrane being inflatable via a liquid when said cannula projects from said sharpened point of said hollow needle in the tissue perforated by said sharpened point to create a cavity in the tissue to be treated, wherein laser radiation is guided by said light guide into said cavity, said liquid containing at least one light scattering medium, said at least one light scattering medium providing uniform irradiation of said balloon.

2. Device according to claim 1, wherein said membrane is extractably housed in the distal end of said cannula.

3. Device according to claim 2, wherein said membrane is housed in a collapsed condition in the distal end of said cannula as said hollow needle is inserted in the tissue, said membrane being inflated with said liquid in an operating state, at least a portion of said inflatable membrane being in contact with an inner surface of said cannula.

4. Device according to claim 3, wherein the outer surface of the cannula is provided with a coating layer having a low coefficient of friction.

5. Device according to claim 2, wherein the outer surface of the cannula is provided with a coating layer having a low coefficient of friction.

6. Device according to claim 1, wherein said membrane is applied on the outer surface of the distal end of said cannula and covers the tip of said cannula.

7. Device according to claim 6, wherein the tip of said cannula is rounded, said inflatable membrane being fixed to said cannula for movement therewith.

8. Device according to claim 7, wherein the outer surface of the cannula is provided with a coating layer having a low coefficient of friction.

9. Device according to claim 6, wherein the outer surface of the cannula is provided with a coating layer having a low coefficient of friction.

10. Device according to claim 1, wherein the outer surface of the cannula is provided with coating layer having a low coefficient of friction.

11. Device according to claim 1, wherein said liquid contains at least one light absorbing medium.

12. Device according to claim 1, wherein said light guide is an optical fiber.

13. Device according to claim 1, wherein said membrane is transparent or translucent to the wavelength of the radiation guided by said light guide.

14. Device according to claim 1, further comprising a circuit for circulating a fluid in said membrane.

15. Device according to claim 1, wherein the terminal end of said light guide is associated with means for converting the light energy to ultrasonic energy.

16. Device according to claim 1, wherein the terminal end of said light guide is associated with an opto-acoustic transducer.

17. A device according to claim 1, wherein heat from said light guide is transmitted to the tissue via said liquid and said membrane.

18. A device according to claim 1, wherein said membrane is in a collapsed state as said hollow needle is inserted in the tissue, said membrane in said collapsed state being located at a position within said hollow needle as said hollow needle is inserted in the tissue.

19. An interstitial tumor laser thermotherapy device, comprising:
    a hollow needle with a sharpened tip, said sharpened tip defining a means for perforating a tissue to be treated;
    a light guide;
    a cannula arranged in said hollow needle, said cannula and said hollow needle being movable relative to one another such that cannula moves from a position within said hollow needle to another position, said cannula extending from said sharpened tip in said another position, said light guide being arranged in said cannula, wherein said cannula is provided with an inflatable membrane which is inflatable via a liquid to form a balloon into which a distal end of said light guide can project, the membrane being housed within said cannula or adherent to said cannula and being inflatable via said liquid when said cannula is in said another position to create a cavity in the tissue to be treated, wherein laser radiation is guided by said light guide into said cavity with said cannula in said another position, said light guide and said membrane being arranged and designed to generate a substantially uniform irradiation of the membrane, once the membrane is inflated via said liquid, said liquid containing at least one light scattering medium, wherein said laser radiation is dispersed via said at least one light scattering medium to provide said substantially uniform irradiation of said membrane.

20. A device according to claim 19, wherein said liquid contains at least one light absorbing medium.

21. A device according to claim 19, wherein said membrane is housed in a collapsed condition in the distal end of said cannula as said hollow needle is inserted in the tissue, said membrane being inflated in an operating state with said hollow needle in an operating state, at least a portion of said inflatable membrane being in contact with an inner surface of said cannula.

22. A device according to claim 19, wherein said membrane is in a collapsed state as said hollow needle is inserted in the tissue, said membrane in said collapsed state being located at a position within said hollow needle as said hollow needle is inserted in the tissue.

23. A device according to claim 19, wherein heat from said light guide is transmitted to the tissue via said liquid and said membrane.

24. A device according to claim 19, wherein a terminal end of said light guide is associated with a means for converting light energy to ultrasonic energy.

25. A device according to claim 19, wherein the terminal end of said light guide is associated with an opto-acoustic transducer.

26. An interstitial tumor laser thermotherapy device, comprising:
   a hollow needle with a sharpened tip, said sharpened tip defining a means for perforating a tissue to be treated;
   a light guide;
   an inflatable membrane;
   a cannula arranged in said hollow needle, said cannula and said hollow needle being movable relative to one another such that cannula moves from a position within said hollow needle to another position, said cannula extending from said sharpened tip in said another position, said light guide being arranged in said cannula, said cannula being connected to said inflatable membrane, said inflatable membrane being arranged in said cannula with said membrane in an uninflated state, said inflatable membrane being inflated via a liquid to form an inflated state of said inflatable membrane, wherein a distal end of said light guide projects into an interior of said inflatable membrane with said inflatable membrane in said inflated state when said cannula is in said another position to create a cavity in the tissue to be treated, wherein laser radiation is guided by said light guide into said cavity with said cannula in said another position, said light guide and said membrane being arranged and designed to generate a substantially uniform irradiation of an entire circumferential inner surface of the inflatable membrane with said inflatable membrane in said inflated state, said liquid containing at least one light scattering medium, wherein said at least one light scattering medium disperses said laser radiation to generate said substantially uniform irradiation of said entire circumferential inner surface with said inflatable membrane in said inflated state.

27. A device according to claim 26, wherein said inflatable membrane is in said uninflated state as said hollow needle is inserted in the tissue, said inflatable membrane in said uninflated state being located at a position within said hollow needle as said hollow needle is inserted in the tissue.

28. A device according to claim 26, wherein at least a portion of said inflatable membrane is in contact with an inner surface of said cannula.

29. A device according to claim 26, wherein a terminal end of said light guide is associated with a means for converting light energy to ultrasonic energy.

30. A device according to claim 26, wherein a terminal end of said light guide is associated with an opto-acoustic transducer.

* * * * *